United States Patent [19]

Shirasaka

[11] Patent Number: 4,945,767
[45] Date of Patent: Aug. 7, 1990

[54] METHOD AND SYSTEM FOR CONTROLLING ULTRASONIC PROBE OPERATION

[75] Inventor: Toshio Shirasaka, Tochigi, Japan

[73] Assignee: Kabushiki Kaisha Toshiba, Kawasaki, Japan

[21] Appl. No.: 402,997

[22] Filed: Sep. 6, 1989

Related U.S. Application Data

[63] Continuation of Ser. No. 146,180, Jan. 20, 1988, abandoned.

[30] Foreign Application Priority Data

Jan. 22, 1987 [JP] Japan .................................. 62-13691

[51] Int. Cl.⁵ ............................................ G01N 29/06
[52] U.S. Cl. ....................................... 73/610; 73/626; 128/661.01
[58] Field of Search .................. 73/609, 610, 611, 612, 73/614, 615, 626, 628; 128/661.01

[56] References Cited

U.S. PATENT DOCUMENTS 4,708,127 11/1987 Abdelghani ...................... 128/24 A Primary Examiner—John Chapman
Attorney, Agent, or Firm—Finnegan, Henderson, Farabow, Garrett and Dunner

[57] ABSTRACT

To reduce the power consumption of the ultrasonic probe, the number of transducers to be driven at any given time is controlled. More specifically, all transducers are driven, whereby the probe transmits the ultrasonic beams to a subject through an acoustic lens provided in front of the probe. When an echo signal reflected from an interior portion of the subject and a multi-echo signal reflected from the acoustic lens are detected, the transducers whose operation is required to obtain a tomographic image of the subject are driven. When only the multi-echo signal is detected, fewer transducers are driven.

6 Claims, 4 Drawing Sheets

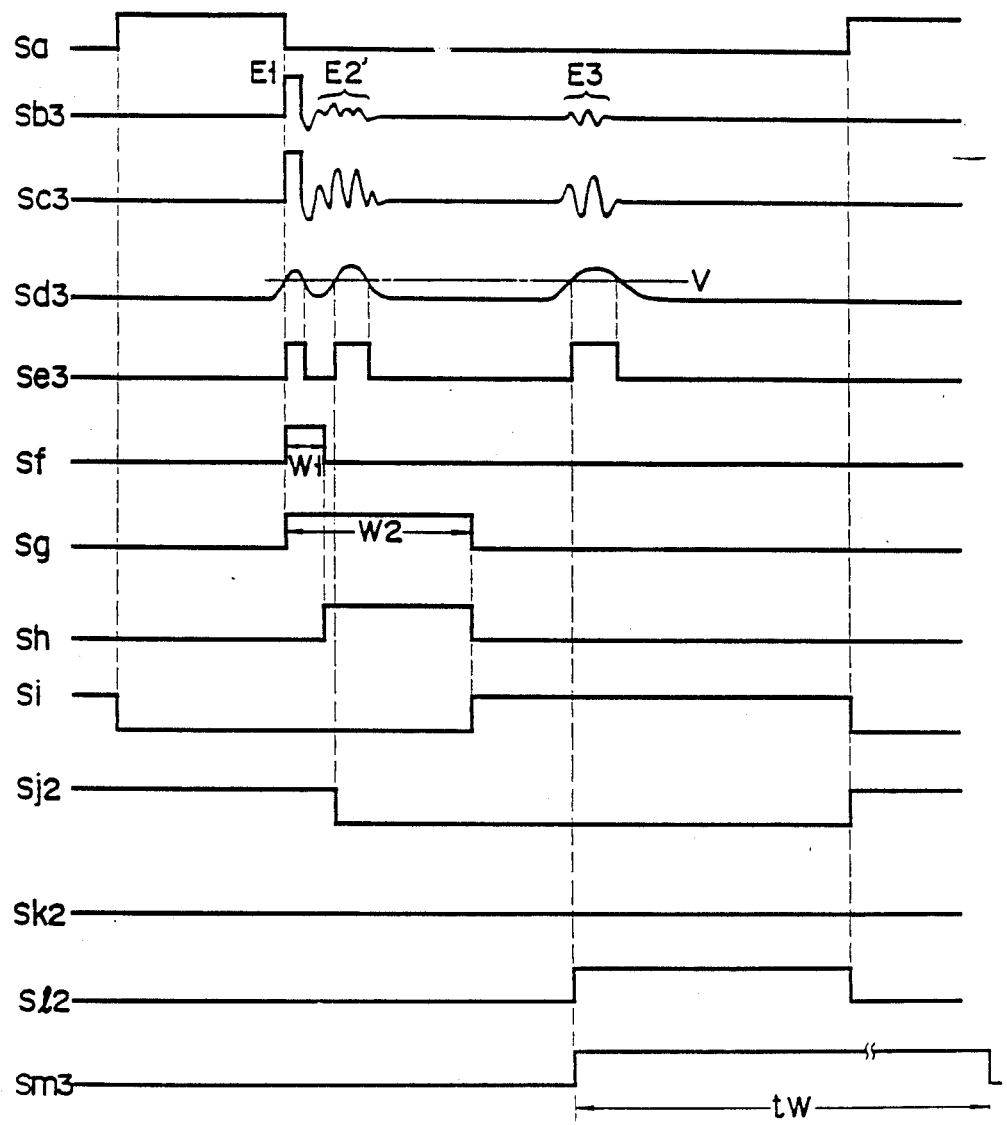
F I G. 2C

METHOD AND SYSTEM FOR CONTROLLING ULTRASONIC PROBE OPERATION

This application is a continuation of application Ser. No. 07/146,180, filed Jan. 20, 1988, abandoned.

BACKGROUND OF THE INVENTION

The present invention relates to an ultrasonic-probe-operation control method and system for controlling the number of transducers—incorporated in an ultrasonic probe—to be driven at any given time.

The transducers incorporated in the probe transmit ultrasonic beams to a subject. These beams are reflected from the subject. The probe detects the reflected beams in the form of echo signals. The echo signals are processed, thereby forming a tomogram of the subject. An idling period elapses between the time the apparatus has been turned on and the time the apparatus starts forming a tomogram of the subject after the probe has been attached to the subject at a desired part. The transducers are driven during this idling period, and hence consume power. The longer the idling period, the more the transducers are heated. The more the transducers are heated, the shorter the lifetime of the transducers.

To prevent the lifetime of the transducers from decreasing, a method has been proposed in which the voltage applied to the transducers is reduced as long as the probe detects no echo signals. The voltage, which is high enough to drive the transducers completely, is applied to the transducers only while the probe is detecting an echo signal. The total power supplied to the transducers is, therefore, smaller than in the case where the high voltage is applied to the transducers all the time the apparatus is turned on.

When this method is applied to the conventional ultrasonic diagnosis apparatus, either the low voltage or the high voltage must be selected instantaneously, for example within the repeating period (about 10 nsec) of an ultrasonic transmitting signal. However, the response characteristic of the apparatus is so poor that such an instantaneous selection of voltage cannot be achieved.

Therefore, there is a reed for a method that can reduce the power consumption of the transducers incorporated in an ultrasonic probe, without switching the voltage applied to the transducers, from one voltage to another.

SUMMARY OF THE INVENTION

The object of this invention is to provide an ultrasonic-probe-operation control method and system for controlling the number of transducers—incorporated in an ultrasonic probe—to be driven at any given time.

According to one aspect of the invention, there is provided a method of controlling the number of transducers to be driven at any given time, the method comprising the steps of:

driving at least one of the transducers;

transmitting an ultrasonic beam generated by the transducer driven, toward a subject, and receiving an echo signal; and outputting a first command signal when the received echo signal includes a multi-echo signal reflected from an acoustic lens, thereby driving at least one transducer, and outputting a second command signal when the received echo signal includes the multi-echo signal and a subject echo signal reflected from the subject thereby driving a plurality of transducers to obtain a tomographic image of the subject.

According to another aspect of this invention, there is provided a system for controlling the number of transducers to be driven at any given time, the system comprising:

a plurality of transducers incorporated in an ultrasonic probe;

means for driving at least one of the transducers to transmit an ultrasonic beam toward a subject and to receive an echo signal; and means for outputting a first command signal to the driving means when the echo signal received by the transducer includes a multi-echo signal reflected from an acoustic lens, thereby driving the at least one transducer, and outputting a second command signal when the echo signal received by the transducer includes the multi-echo signal and a subject echo signal reflected from the subject, thereby driving the plurality of transducers to obtain a tomographic image of the subject.

BRIEF DESCRIPTION OF THE DRAWINGS

FIGS. 2A to 2C are timing charts illustrating the waveforms of signals which are output from the main components of the system, in accordance with the states of a probe.

DETAILED DESCRIPTION OF THE PREFERRED EMBODIMENT

The embodiment of this invention will now be explained, with reference to the accompanying drawings.

Figure 1:
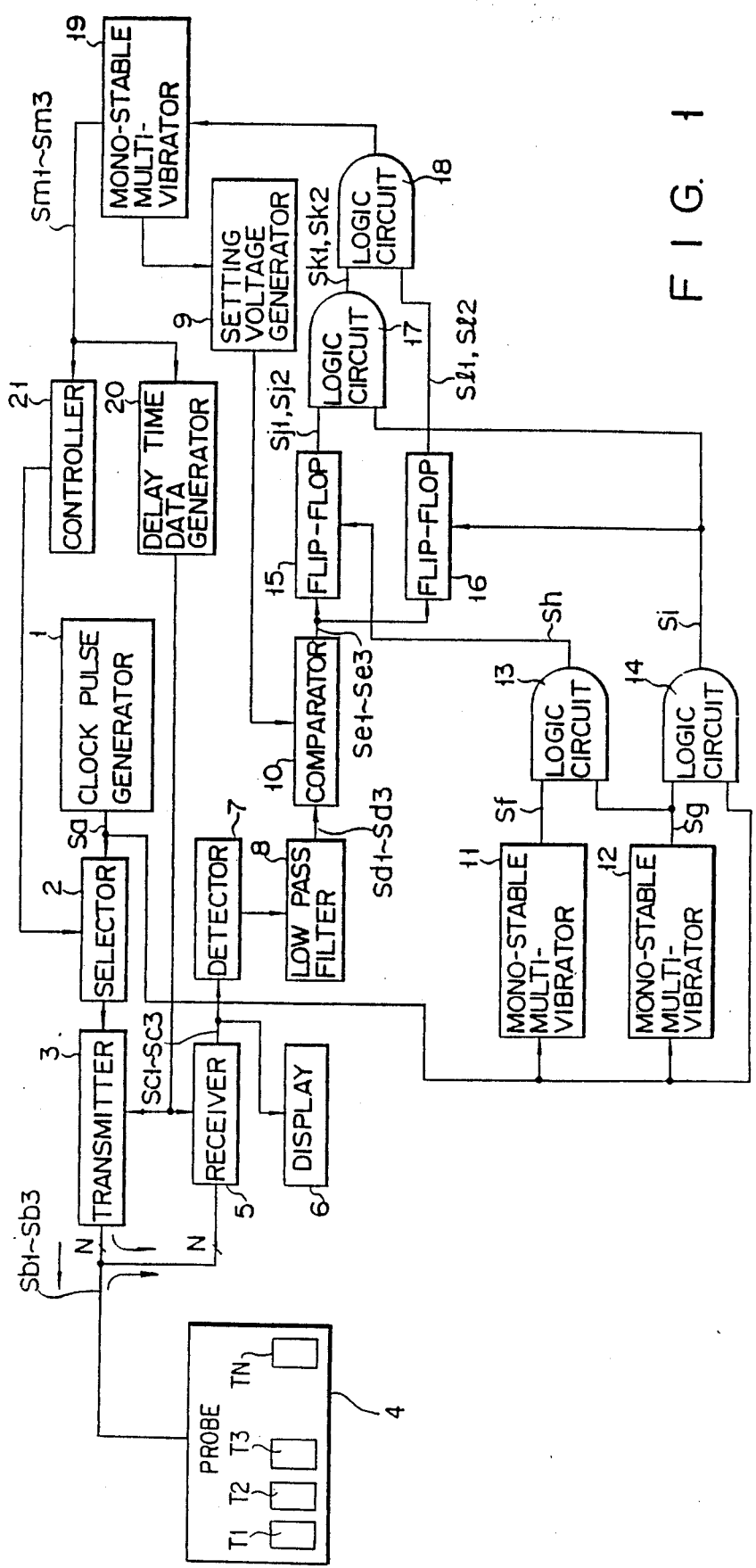
FIG. 1 is a block diagram of an ultrasonic probe-controlling system according to the embodiment of this invention.
Figure 2A:
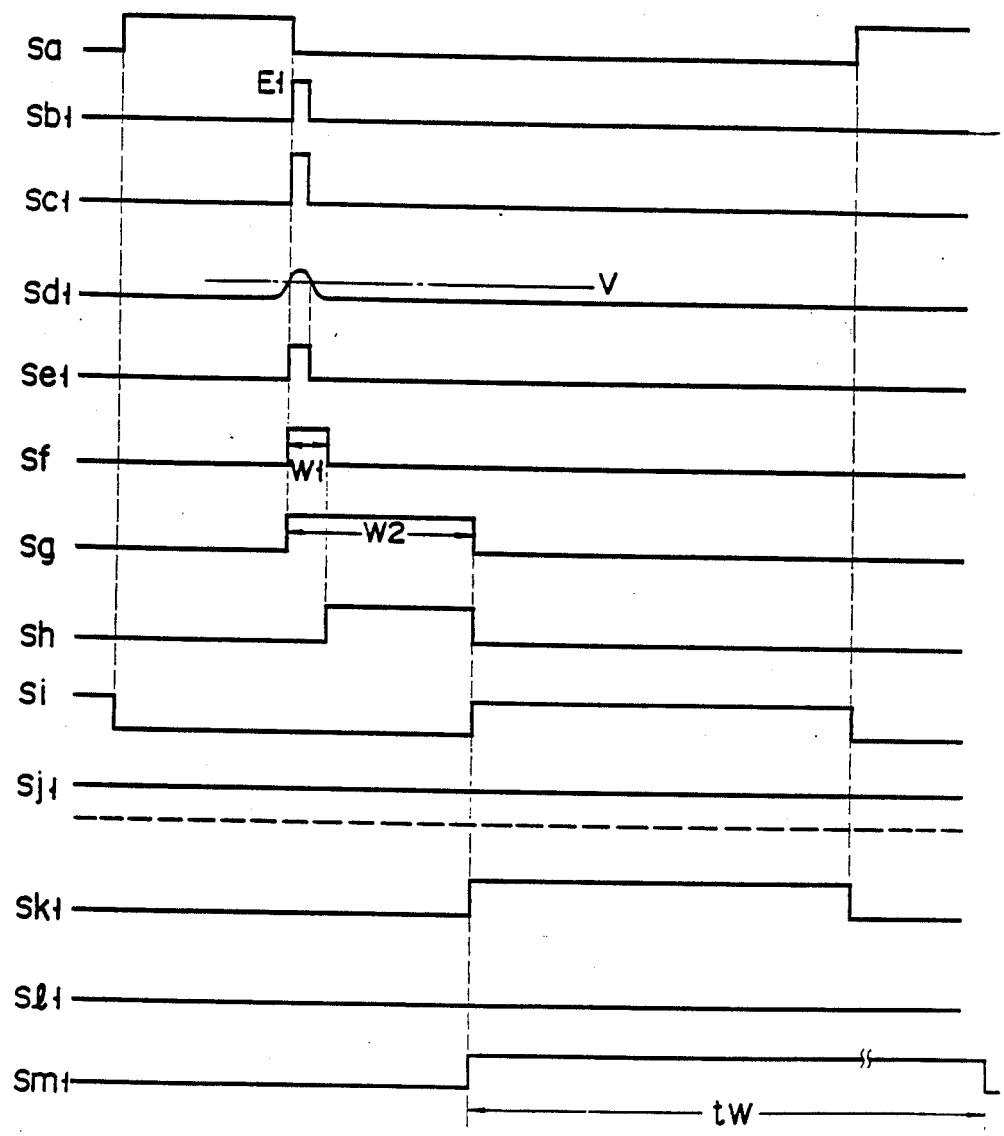
Figure 2B:
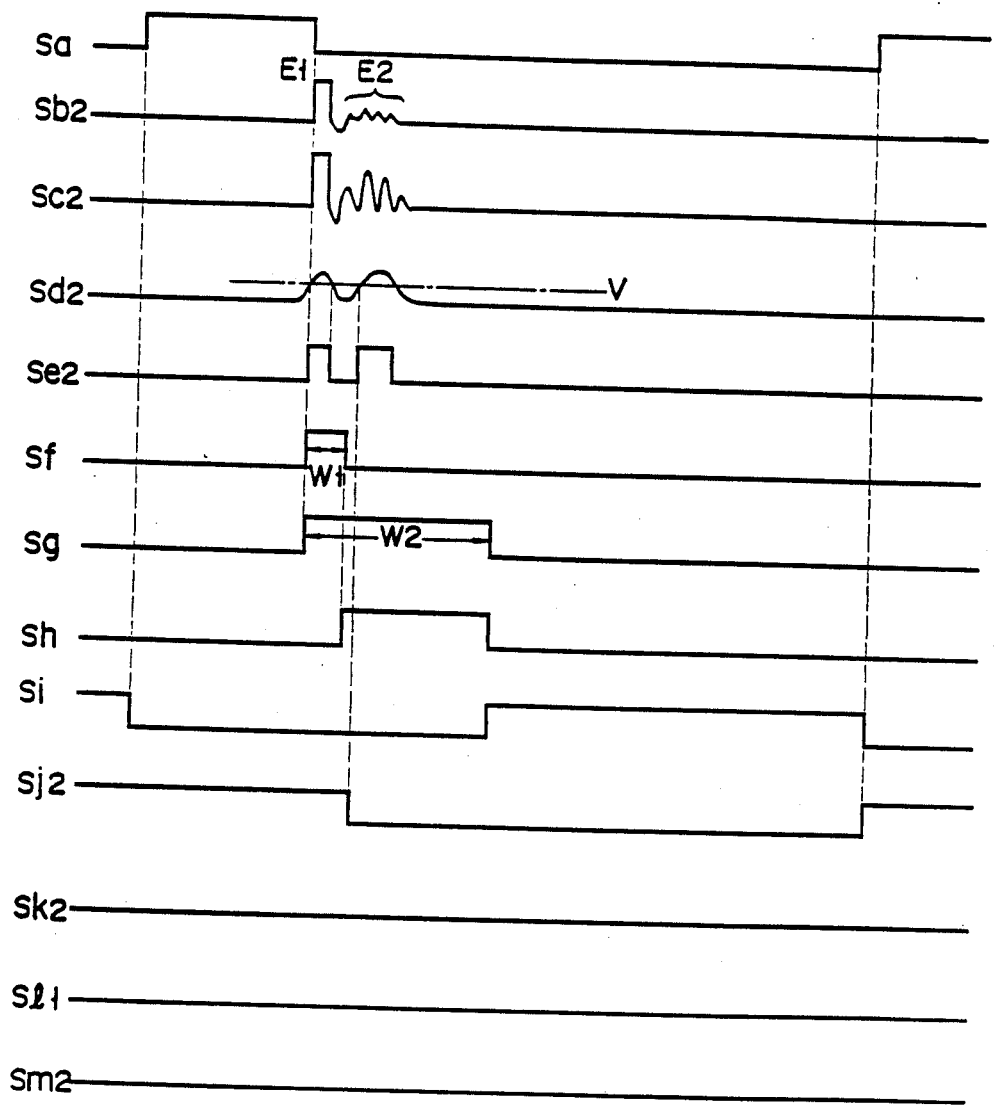

As is shown in FIGS. 1 and 2A to 2C, clock pulse generator 1 generates clock pulse signals Sa. Signal Sa is supplied through selector 2 to transmitter 3 having N transmitting pulse generators. Transmitter 3 is also supplied with delay time data from delay time data generator 20. Ultrasonic probe 4 has a plurality of transducers T1, T2, T3, ... TN. Controller 21 controls selector 2 tc drive the plurality of transducers T1, T2, T3, ..., TN by supplying clock pulse signals Sa to probe 4.

Like most existing probes, probe 4 contains several tens of transducers. Pulse signals E1 having various delay times are supplied to these transducers. Hence, the transducers are driven by signals E1 at various times, whereby probe 4 transmits an ultrasonic beam. An acoustic lens which has a predetermined acoustic impedance is provided in front of probe 4, for deflecting or converging the ultrasonic beam transmitted from probe 4.

Various echo signals are detected by probe 4, depending on the condition in which probe 4 is used. More specifically:

(1) When the front of probe 4 is in contact with the liquid contained in a test tank, probe 4 detects only a pulse signal E1 of Sb1. (See FIG. 2A.) The liquid has the same acoustic impedance with the acoustic lens. No test pieces are immersed in the liquid.

(2) When probe 4 contacts neither a subject nor the liquid contained in the test tank, it detects a transmitting pulse signal E1 of Sb2 and a multi-echo signal E2 of Sb2, which has been generated by the acoustic lens. (See FIG. 2B).

(3) When probe 4 is in contact with the surface of a subject, it detects a transmitting pulse signal E1 of Sb3, an echo signal E2′ of Sb3 reflected from the surface of the subject and from the acoustic lens, and an echo signal E3 of Sb3 reflected from the interior of the subject. (See FIG. 2C.)

When, in case (2), transmitting pulse signal E1 is input to probe 4 from transmitter 3 at the trailing edge of clock pulse signal Sa, multi-echo signal E2 is generated. In case (3), when pulse signal E1 is transmitted from probe 4, echo signal E3 is reflected from the interior of the subject, and signal E2' including a multi-echo signal generated by the acoustic lens and an echo signal reflected from the surface of the subject, is generated. Receiver 5 receives signals E1, E2, E2', and E3. These signals are amplified. The amplified signals Sc1 to Sc3 are displayed on display 6. The amplified signals are detected by detector 7 and input to low pass filter 8. Filter 8 removes the high frequency components of signals Sc1 to Sc3, thereby outputting signals Sd1 to Sd3. Comparator 10 compares signals Sd1 to Sd3 with a predetermined voltage V generated by setting voltage generator 9, and outputs pulse signals Se1 to Se3 having the same widths as the widths which signals Sd1 to Sd3 have at voltage V. Signals Se1 to Se3 are input to flip-flops 15 and 16.

Upon the input of clock pulse signal Sa, mono-stable multivibrator 11 generates a pulse signal Sf having a predetermined width W1 which corresponds to the range of transmitting pulse signal E1. Upon the input of clock pulse signal Sa, another mono-stable multivibrator 12 generates a pulse signal Sg having a predetermined width W2 which corresponds to the range of transmitting pulse signal E1 and multi-echo signal E2. Signals Sf and Sg are input to logic circuit 13. Upon receiving of signals Sf and Sg, logic circuit 13 outputs a signal Sh which indicates the period within which multi-echo signal E2 has been generated. Signal Sh will be used to determine whether or not multi-echo signal E2 is generated.

Upon the input of signal Se1, Se2 or Se3 and signal Sh, flip-flop 15 outputs a signal Sj1 or Sj2, while flip-flop 16, upon the input of signal Se1, Se2 or Se3 and signal Si, outputs a signal Sl1 or Sl2. Logic circuit 17 receives signal Si and signal Sj1 or Sj2, and outputs a signal Sk1 or Sk2. The waveform of signal Sk1 rises at the leading edge of signal Si when only transmitting pulse signal E1 has been detected.

Upon the input of signal Sk1 or Sk2 and signal Sl1 or Sl2, logic circuit 18 generates a signal, which is supplied to mono-stable multivibrator 19. Multivibrator 19 outputs signals Sm1, Sm2 or Sm3 to controller 21, delay time data generator 20, and voltage generator 9, respectively, during a predetermined period $t_W$. The output signal of multivibrator 19 varies in accordance with output signal Sk1 or Sk2 of logic circuit 17 and output signal Sl1 or Sl2 of flip-flop 16.

When probe 4 is in contact with the surface of the subject, echo signal E3, reflected from the interior of the subject, is detected, thus the output signal of multivibrator 19 is at a high level (Sm3). As a result, controller 21 controls selector 2 to drive the plurality of transducers used to obtain a tomographic image of the subject. In this case, with probe 4 in contact with the surface of the subject, transmitter 3 drives those transducers required for obtaining a tomographic image. On the other hand, when probe 4 is not in contact with either the liquid or the subject; multi-echo signal E2 is detected, thus the output signal of multivibrator 19 is at a low level (Sm2). As a result, controller 21 controls selector 2 to drive for example one or two transducers.

To prevent the diagnosis apparatus from malfunctioning when probe 4 is instantaneously removed from the surface of the subject, time period $t_W$ of signals Sm1 and Sm3 is relatively long, for example, several seconds. When the signal output from mono-stable multivibrator 19 is at a low level, voltage V output from setting voltage generator 9 is reduced.

The operation of the control system according to this embodiment will now be explained.

When probe 4 is in contact with the surface of the subject, probe 4 detects echo signal E3 reflected from the interior of the subject, and signal E2' including multi-echo signal and the echo signal reflected from the surface of the subject. In this case, signal Sm3 at the high level, output from multivibrator 19, is input to controller 21. Consequently, those transducers whose operation is required to obtain a tomographic image are driven by transmitter 3. When a predetermined period has elapsed following the removal of probe 4 from the surface of the subject, probe 4 can no longer detect echo signal E3 reflected from the interior of the subject; it can detect only multi-echo signal E2 generated by the acoustic lens. Consequently, the low-level signal Sm2 output from mono-multivibrator 19 is input to controller 21. As a result, with probe 4 not in contact with either the liquid or the subject, one or more transducers fewer than those whose operation is required to obtain a tomographic image are driven.

As described above, voltage V generated by voltage generator 9 is applied to comparator 10 for comparison with received echo signals. With respect to the case in which the number of transducers to be driven is decreased by signal Sm2 output from multivibrator 19, there is a corresponding decrease in the echo signal magnitude received by probe 4 and the echo signal is detected by decreasing the voltage level generated by setting voltage generator 9. With respect to the case in which the number of transducers to be driven is increased by signal Sm3 output from multivibrator 19 to obtain a tomogram image, there is a corresponding increase in the echo signal magnitude received by probe 4 and the echo signal is detected by increasing the voltage level generated by setting voltage generator 9. That is, the voltage level generated by the setting voltage generator is decreased by signal Sm2 and increased by signal Sm3.

As has been described, according to this embodiment, when probe 4 is removed from the surface of the subject so that it is not in contact with either the liquid or the subject, a pulse signal is supplied to, for example, only one transducer or the transducers fewer than those whose operation is required to obtain a tomographic image of the subject. This reduces the power consumption of the system, though the voltage applied to the transmitter is not controlled at all. In addition, the number of transducers which should be driven at any given time can be selected, and some of the transducers, which are at desired positions, can be selected, and the time at which each transducer should be driven can be predetermined.

The present invention is not limited to the above-explained embodiment, but can be modified in various ways within the scope and spirit thereof.

What is claimed is:

1. A method for controlling the number of transducers to be driven in an ultrasonic probe, the method comprising the steps of:

driving at least one of the transducers;

transmitting an ultrasonic beam generated by the transducer driven, and receiving an echo signal; and outputting a first command signal when the received echo signal includes a multi-echo signal reflected from an acoustic lens, thereby driving at least one transducer, and outputting a second command signal when the received echo signal includes the multi-echo signal and a subject echo signal reflected from an interior portion of a subject, thereby driving a plurality of transducers to obtain a tomogram image of the subject, the number of transducers driven by the first command signal being fewer than the number of transducers driven by the second command signal.

2. The method according to claim 1, wherein delay time data is generated by detection of the subject echo signal reflected from the subject; and said driving step includes the substep of generating pulse signals for driving said transducers in accordance with the delay time data.

3. The method according to claim 1 including the additional steps of:

generating, in response to said first or second command signal, a voltage value used to detect the echo signal; and comparing the echo signal with the generated voltage value to detect the echo signal.

4. A system for controlling the number of transducers to be driven in an ultrasonic probe, the system comprising:

a plurality of transducers incorporated in the ultrasonic probe;

driving means for driving at least one transducer to transmit an ultrasonic beam toward a subject, and to receive an echo signal; and outputting means for outputting a first command signal to the driving means when the echo signal received by the transducer includes a multi-echo signal reflected from an acoustic lens, thereby driving the at least one transducer, and outputting a second command signal to the driving means when the echo signal received by the transducer includes the multi-echo signal and a subject echo signal reflected from an interior portion of the subject, thereby driving the plurality of transducers to obtain a tomogram image of the subject, the number of transducers driven by the first command signal being fewer than the number of transducers driven by the second command signal.

5. The system according to claim 4, further comprising means for generating delay time data by detection of the subject echo signal reflected from the subject, and for supplying the delay time data to the driving means, said driving means outputting pulse signals for driving said transducers in accordance with the delay time data.

6. The system according to claim 4, further including means, responsive to said first and second command signals, for generating a voltage value used to detect the echo signal; and means for comparing the echo signal with the generated voltage value to detect the echo signal.

* * * * *